United States Patent [19]

Schuller et al.

[11] Patent Number: 4,941,164
[45] Date of Patent: Jul. 10, 1990

[54] METHOD AND APPARATUS FOR IMPROVING THE ALIGNMENT OF RADIOGRAPHIC IMAGES

[75] Inventors: Paul D. Schuller, Edmonton, Canada; David C. Hatcher, Sacremento, Calif.; Terrance M. Caelli, Edmonton, Canada; Frank M. Eggert, Edmonton, Canada; Jerome Yuzyk, Edmonton, Canada

[73] Assignee: The Governors of the University of Alberta, Edmonton, Canada

[21] Appl. No.: 150,242

[22] Filed: Jan. 29, 1988

[30] Foreign Application Priority Data

Oct. 29, 1987 [CA] Canada ............................... 550585

[51] Int. Cl.$^5$ .................................................. A61B 6/08
[52] U.S. Cl. .................................... 378/205; 378/168; 378/177; 378/207; 378/99
[58] Field of Search ................... 378/22, 38–40, 378/168–170, 204–205, 99, 207, 162, 164, 163; 358/111

[56] References Cited

U.S. PATENT DOCUMENTS

| | | | |
|---|---|---|---|
| 2,753,461 | 7/1956 | Goldberg | 378/170 |
| 3,283,071 | 11/1966 | Rose et al. | 378/204 |
| 3,714,428 | 1/1973 | Gasaway | 378/163 |
| 3,777,141 | 12/1973 | Eggen | 378/170 |
| 4,262,306 | 4/1981 | Renner | 358/111 |
| 4,409,616 | 10/1983 | Ledley | 378/99 |
| 4,564,861 | 1/1986 | Hishimura et al. | 358/111 |
| 4,633,493 | 12/1986 | Linden | 378/170 |
| 4,700,058 | 10/1987 | Belanger et al. | 378/99 |
| 4,701,875 | 12/1987 | Nakajima et al. | 358/111 |
| 4,707,847 | 11/1987 | Van Aken | 378/169 |
| 4,736,399 | 4/1988 | Okazaki | 378/99 |

FOREIGN PATENT DOCUMENTS 0405536 11/1973 U.S.S.R. ............................... 378/170

OTHER PUBLICATIONS

"Spiral Analysis Using a 3 Dimensional Radiographic Technique", by Brown et al., J. Biomechanics, vol. 9, 1976.

Primary Examiner—Craig E. Church
Assistant Examiner—John C. Freeman
Attorney, Agent, or Firm—Sim & McBurney

[57] ABSTRACT

In a diagnostic process in which two images are made on an image recording medium of the same structure at the beginning and the end of a time interval during which the structure changes, a method is provided for permitting a computing device to improve the alignment of the images as reproduced in the form of pixels on a monitor screen. A particular spatial pattern of marker elements is provided, when each of the images is made, in a particular juxtaposition to the structure being imaged, so that the shadows of the elements arise on the respective images. The computing device can then rotate, translate and alter the scale of one image with respect to the other until the shadows of the elements on one image coincide as closely as possible with those on the other image.

13 Claims, 9 Drawing Sheets

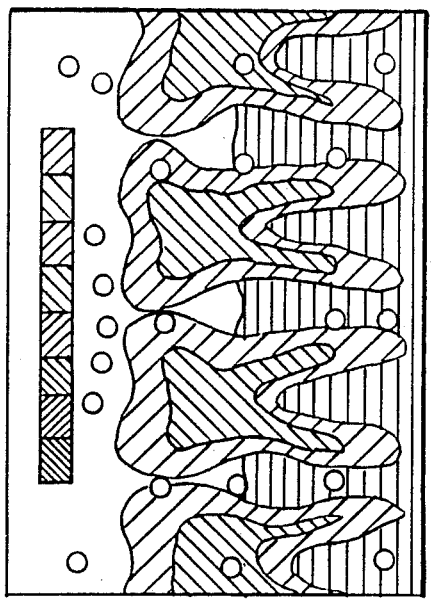
FIG. 5(a) IMAGE 1
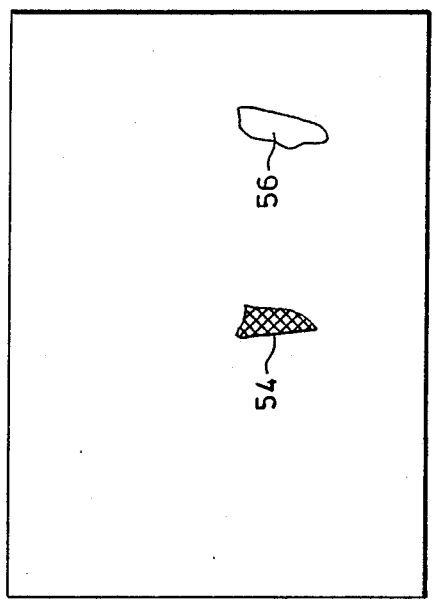
FIG. 5(c) IMAGE 3
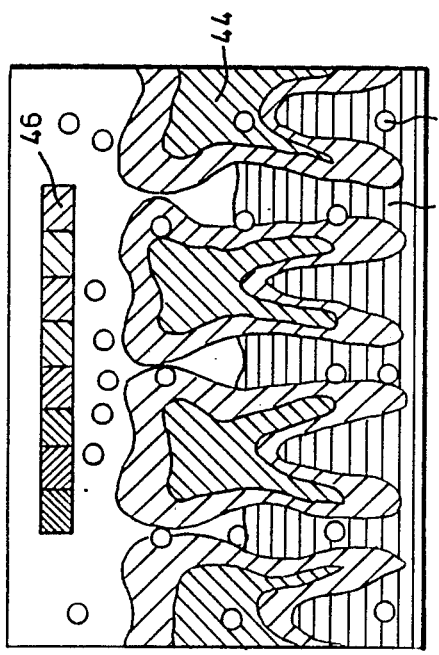
FIG. 5
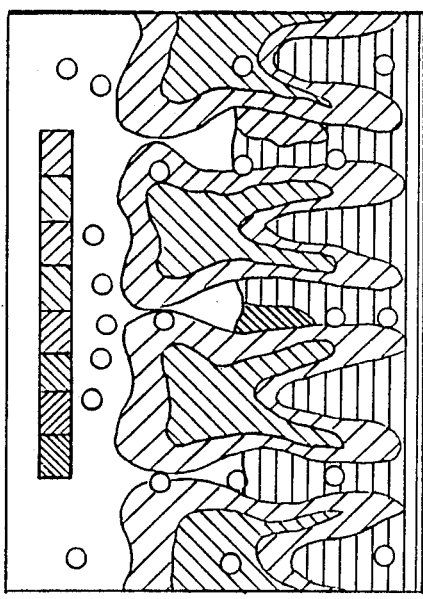
FIG. 5(b) IMAGE 2

FLOW-CHART 1: IMAGE DIGITISATION AND CHARACTERIZATION

FLOW CHART 2: SPATIAL TRANSFORMATION FOR ALIGNMENT

FLOW CHART 4. IMAGE COMPARISON

FLOW CHART 5: DIFFERENCE QUANTIFICATION

METHOD AND APPARATUS FOR IMPROVING THE ALIGNMENT OF RADIOGRAPHIC IMAGES

This invention relates generally to the field of radiology, and has to do particularly with a method and apparatus for improving the alignment of radiographic images taken at different times of the same tissue structure, so that the images can be sequentially shown in aligned condition, whereby changes in the structure can be noted.

BACKGROUND OF THIS INVENTION

The present invention will be described specifically in connection with dental radiology and its use in determining on-going structural changes in teeth and related structures (such as remineralization). However, it will be understood from what follows that the principles of this invention could be applied in other areas.

It is known to utilize a computer to carry out densitometric analyses of standardized radiographs taken of the same tissue structure at different points in time, in order to detect tissue change. For example, in the dental area it is known to compare radiographs of the same tooth structure taken at different times, in order to detect remineralization in the teeth or lesions in the periodontal tissue. One technique utilized in this procedure is called subtraction radiography, wherein a computer will digitize two standardized radiographs of the same structure taken at different times, and then subtract the one from the other. If the two radiographs are identical, the result will be a uniform picture with no apparent detail. However, if the radiographs differ, for example at anatomical locations which have changed between the exposures, then the subtraction image will exhibit a different density (grey level) than the background. The above principles are well understood, and form part of the prior art. Reference may be made to an article entitled "Subtraction Radiography and Computer Assisted Densitometric Analyses of Standardized Radiographs", by Ortman et al, published in the Journal of Periodontal Research, 1985: 20:644–651.

Thus, it will be understood that, when wishing to compare radiographic images taken at different times of the same dental structure for the purpose of following changes in the structure, the ideal situation is that in which both or all of the images are made under precisely the same conditions of exposure. In other words, for every image, the relative positions of the film, the teeth and the source of X-rays would be identical. Moreover, the degree of exposure, the film characteristics, and the intensity of the X-ray source would also have to be the same from exposure to exposure. If this could be achieved consistently, then subtraction radiography could be carried out directly and the information thus generated would be highly reliable.

However, as a practical matter the perfection of alignment is generally not attained. Although a bite block of conventional nature can be utilized to ensure to a large degree that the position of the film with respect to the teeth is consistent from image to image, it will be appreciated that even a slight change in the geometric position of the source of the X-rays from image to image (further or closer, up or down, right or left) will significantly alter the scale or position of the image by an amount sufficient to interfere with analysis of structural changes by the technique of subtraction radiography. Furthermore, where the film is improperly inserted into the bite block, sequential images can be mutually rotated even where the source of the X-ray is precisely the same.

Conventionally, attempts have been made to overcome the alignment problem by utilizing external beam-image receptor alignment devices that are very cumbersome and problematic to use. Reference may be had to an article by McHenry et al, entitled "Methodological Aspects and Quantitative Adjuncts to Computerized Subtraction Radiography", published in the Journal of Periodontal Research 1987; 22: 125–132. Even with such devices, however, problems can persist in attaining perfect alignment. For example, problems arising through improper film insertion into a bite block are not overcome by the external alignment devices. And of course, such devices do not address the problem of attaining gray-scale uniformity.

GENERAL DESCRIPTION OF THIS INVENTION

In view of the difficulties and problems outlined above, it is an object of one aspect of this invention to make use of modern microprocessor capabilities to improve the alignment of radiographic images. More specifically, this invention involves the provision of a plurality of marker elements in a specific, repeatable spatial juxtaposition with respect to the animal tissues being investigated (for example the teeth), such that the radiographic images contain the shadows of the marker elements. The radiographic images thus produced are converted to arrays of pixels and stored electronically. Each pixel has a pair of geometric coordinates and also an index number identifying its grey level. The microprocessor or computing device then operates on one of the pixel arrays by first identifying the shadows of the marker elements, and then bringing the geometric coordinates of the marker element shadows on one array into substantially overlying relationship with the geometric coordinates of the marker element shadows on the other array, using translation, rotation, scaling up, scaling down, differential scaling, or a combination of these spatial transformations. By incorporating an aluminum step wedge in association with the marker elements, such that the image of the step wedge also appears on the radiograph, the computer can internally adjust the gray-scale of the various pixels in order to balance the shading in the different radiographs. This is carried out in two separate processes. First, the complete images are corrected for differences in contrast using either a pseudosigmoidal function or other parametric functions or non-parametric approaches. Then, the images of the steps of the wedge are used to construct a calibration curve to convert levels of radiographic density into equivalent weights of hydroxypatite mineral of bone. In this way, changes in radiographic density can be converted into equivalent changes in bone density. Any structural changes can then be determined by subtraction radiography carried out by the computer.

Even more particularly, this invention provides a method for investigating changes in animal tissues, which are within or close to human teeth, comprising:

at a first point in time, providing a bite block containing a plurality of spherical marker elements in a specific, 3-dimensional spatial arrangement, said bite block being gripped in a reproducible fashion at a given location between the teeth so as to ensure that the marker elements achieve a repeatable, 3-dimensional juxtaposition with respect to the tissues, and making a first radiographic image of the tissues by exposing a first photosensitive film to X-ray radiation that has first passed through both the tissues and the marker elements, so that the shadows of the marker elements appear superimposed on the first image of the tissues, at a later point in time, causing the bite block to be gripped again in said reproducible fashion at said given location between the teeth so as to ensure that the marker elements achieve the same 3-dimensional juxtaposition with respect to the tissues, and making a second radiographic image of the tissues by exposing a second photosensitive film to X-ray radiation that has first passed through both the tissues and the marker elements, so that the shadows of the marker elements appear superimposed on the second image of the tissues, converting the first and second images to first and second arrays of pixels and storing the pixel arrays electronically in a memory means, wherein each pixel has a pair of geometric coordinates and also an index number identifying its grey level, using a computing device to improve the alignment of one array of pixels with respect to the other, wherein the computing device identifies the shadows of the marker elements in the two pixel arrays, and operates on one array in such a way as to bring the geometric coordinates of the shadows on one array into the closest possible coincidence with the geometric coordinates of the shadows on the other array, by causing said one array to undergo one or more of the operations of:
(a) translation,
(b) rotation,
(c) scaling up,
(d) scaling down,
(e) differential scaling, storing the improved pixel array electronically in the memory means, and assessing the intensity differences between pairs of corresponding pixels in the improved array and the said other array to determine whether tissue change is indicated.

Further, this invention provides, in a diagnostic process for tissue structure in or close to human teeth, in which two x-ray images are made on photosensitive film of the same structure at the beginning and the end of a time interval during which the structure may change, a method of permitting a computing device which electronically stores the images to perform operations on the images as reproduces in the form of pixels on a monitor screen, each pixel having a specific grey level, the method comprising providing, when each of the images is made, a particular 3-dimensional spatial pattern of spherical marker elements in a particular juxtaposition to said structure so that the shadows of the elements arise on the respective images, the said juxtaposition being the same for each image, the marker elements being separated balls incorporated in a bite block, the X-radiation passing in order through the teeth, the marker elements, and the film.

Finally, this invention provides, for a diagnostic process in which two radiographic images are made on radiographic film of the same human tissues within or close to the teeth at the beginning and the end of a time interval during which tissue change may occur, a bite block for permitting a computing device which electronically stores the images to perform operations on the images as reproduced in the form of pixels on a monitor screen, each pixel having a specific grey level, the bite block registering repeatably with the same teeth of a given person and incorporating a specific, 3-dimensional spatial pattern of spherical marker elements so that when the bite block is held between the given person's teeth the elements will have a specific and repeatable juxtaposition with respect to the dental structure and the shadows of the elements will arise on the respective radiographic films.

GENERAL DESCRIPTION OF THE DRAWINGS

One embodiment of this invention will be described with reference to accompanying drawings, in which like numerals denote like parts throughout the several views, and in which:

FIG. 5 is a face view of an exposed processed film in accordance with this invention;

Figure 1A:
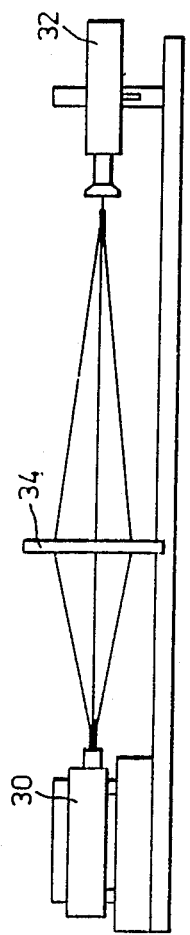
FIG. 1A shows a side view and FIG. 1B shows a top view of digitizing apparatus for use with the method of this invention.

FIGS. 5(a), (b) and (c) represent, respectively, a pre-lesion X-ray image, a post-lesion X-ray image, and a subtraction image made after spatial and intensity alignment; and FIGS. 6 through 10 contain logic flow-charts giving an overview of the program steps carried out in connection with this invention.

DETAILED DESCRIPTION OF THE INVENTION

As has been explained above, the aim of this invention is to provide a means of recording markers on diagnostic images so that images obtained on successive occasions may be analyzed and operated on by a computer or microprocessor in order to provide accurate alignment of the separate images through calculations performed by the computer. In addition to the alignment function, however, the computer can also be utilized to enhance the images, and to carry out a diagnostic analysis of the image in order to provide evidence of and quantification of changes or differences between the successive images.

Essentially, the markers are placed on the diagnostic images by interposing a plurality of marker elements in the beam of a diagnostic imaging system, in such a way that the shadows of the markers are recorded on the image of the anatomical structures that are of diagnostic interest. These marker images or shadows provide a permanent record, in the image, of the positional relationship between (1) the source of the diagnostic radiation for the imaging system, (2) the anatomical structures of interest, (3) the markers themselves, and (4) the recording medium for the diagnostic image.

It is important to understand that the source of the diagnostic radiation for the imaging system can take a number of forms not restricted to diagnostic dental X-rays. Any imaging system will be able to carry out the principle of this invention so long as an image of the markers is formed by the system.

While dental X-ray film is described below in connection with the specific embodiment disclosed in the drawings, it is well known to form images xerographically or even directly in the electronic components of a camera system which is sensitive to diagnostic radiation without the intermediate step of forming an image on X-ray film.

It is further to be understood that the use of markers is of general application in the head and neck region, and is not restricted to intra-oral use. Indeed, the basic principle of this invention (as set out in claim 1, for example) is not even restricted to human or animal tissues. The principle can be applied in any structure which evidences change over a time interval and of which images can be made by passing radiation through it or reflecting radiation off it (e.g., the markers could be white dots on an engine part, imaged conventionally). In the case of the human being, the teeth can be used as fixed reference points for extra-oral as well as intra-oral diagnostic imaging. Other fixed points of the skeleton of the head, such as the oral meati and the bridge of the nose, can also be used as reference points.

Figure 2:
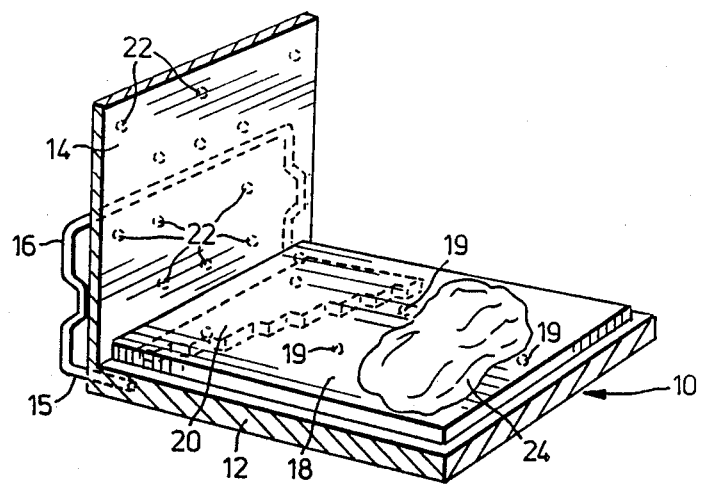
FIG. 2 is a perspective view of a bite block for use with this invention.
Figure 3:
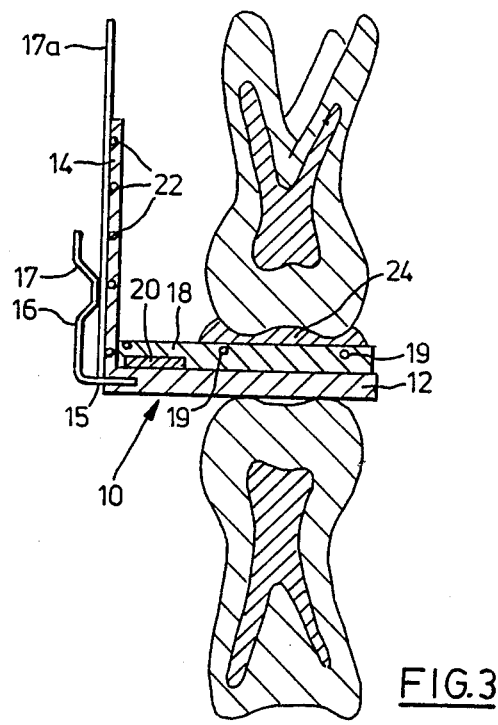
FIG. 3 is a cross-sectional view through the bite block shown in FIG. 2, also illustrating the position of teeth with respect to the bite block.
Figure 4:
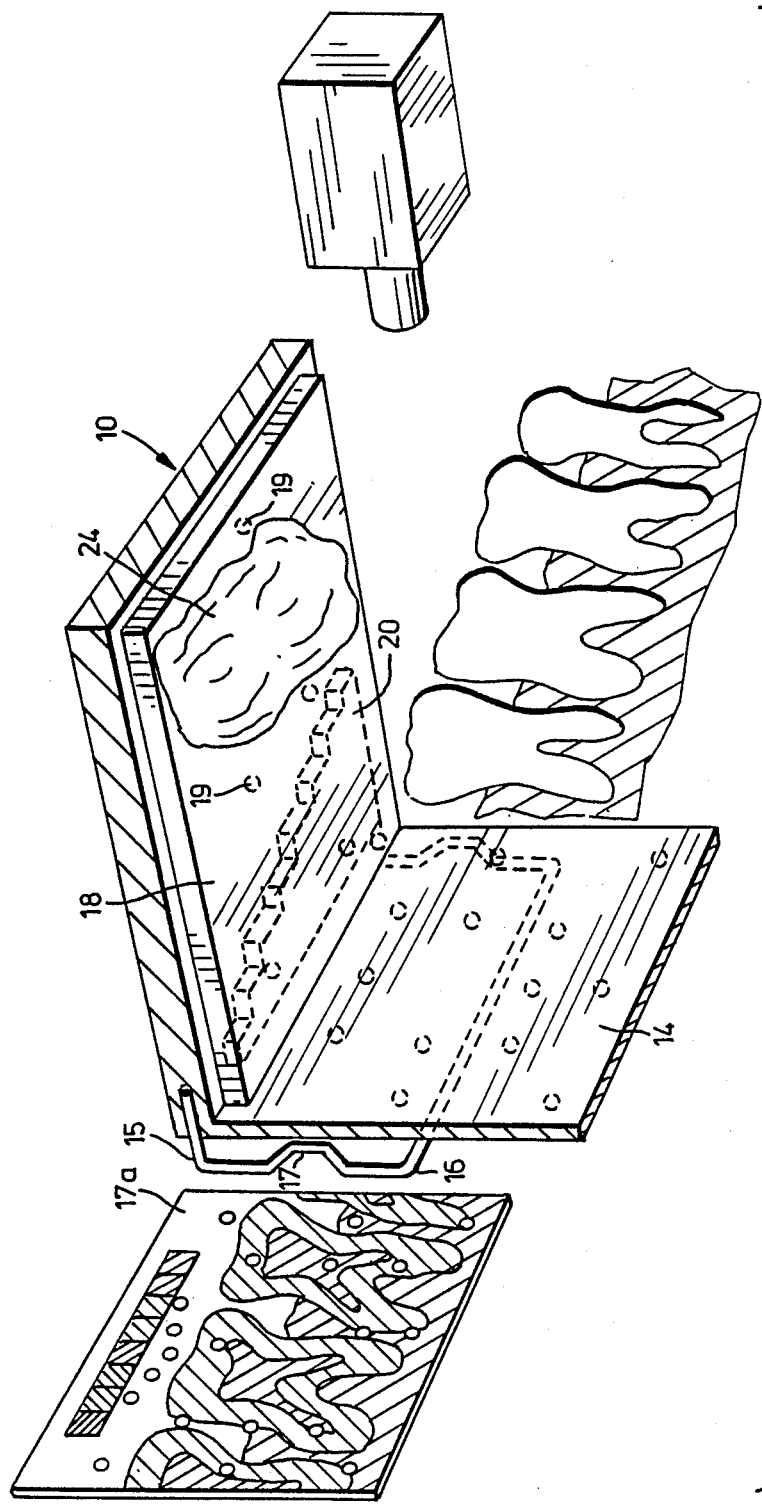
FIG. 4 is an exploded view showing the X-ray source, several teeth, the bite block of FIG. 2 (inverted) and a piece of X-ray film.

Turning first to FIGS. 2, 3 and 4, a bite block 10 constructed in accordance with this invention includes a clamp portion 12 which is connected to a wall 14 extending substantially perpendicularly therefrom. Embedded in the end of the clamp portion 12 which is connected to the wall 14 are the two ends 15 of a film clip 16. The film clip 16 includes a substantially rectangular loop of wire having two portions 17 which are offset toward the wall 14, in order to grip a film holder. In FIG. 3, the film itself is shown at 17a, but of course it will be understood that the film must be protected from exposure to light up to the point of its development. For this purpose, a standard plastic envelope would typically be provided, of a kind well known in the art. Thus, the offset portion 17 of the film clip 16 would press the film envelope against the back of the wall 14, thus holding the film 17a itself in close juxtaposition with the back of the wall 14.

The clamp portion 12 has a further layer 18 superimposed thereon, the purpose of the layer 18 being to contain a plurality of reference balls 19, and a step wedge 20. The step wedge is a block of aluminum cut into discrete steps which present a radiographic "face" of 1, 2, 3, 4 . . . 8 mm thickness, forming (roughly) equal-shaped and equal-sized squares on the image. Additional reference balls 22 are embedded in the wall 14, the pattern being well seen in FIGS. 2 and 4.

Also shown in FIGS. 2 through 4 is a quantity of bite impression material 24 which is of conventional nature and well known in the art. This material is placed on the layer 18 in a somewhat plastic condition, whereupon the patient bites the bite block, holding the teeth in contact with the material 24 until the latter has set. This leaves an impression of the specific teeth in the material 24, which permits the bite block to be precisely relocated in clamped position between the patient's teeth for a series of subsequent X-rays. Thus it will be appreciated that the bite block shown in FIGS. 2–4 allows for the reference balls 19 and 22 to have a specific and repeatable juxtaposition with respect to the same dental structure (teeth and periodontal tissues), and the shadows of the balls 19 and 22 will appear on each radiographic film 17a. The balls 19 and 22 are preferably of lead, although any material could be used, so long as it left a clearly discernable shadow on the radiographic film.

It will thus be appreciated that, by preparing two radiographic images on suitable film or other medium at the beginning and the end of a time interval during which the tooth structure changes (for example by remineralization, lesion or decay), it will be possible firstly to convert each image to an array of pixels each having a specific geometric position and a specific grey level, whereby a computer or microprocessor will be enabled to rotate, translate and/or alter the scale of one image with respect to the other until the shadows of the marker elements on one image substantially coincide with those on the other image.

Digitizing

Figure 1B:
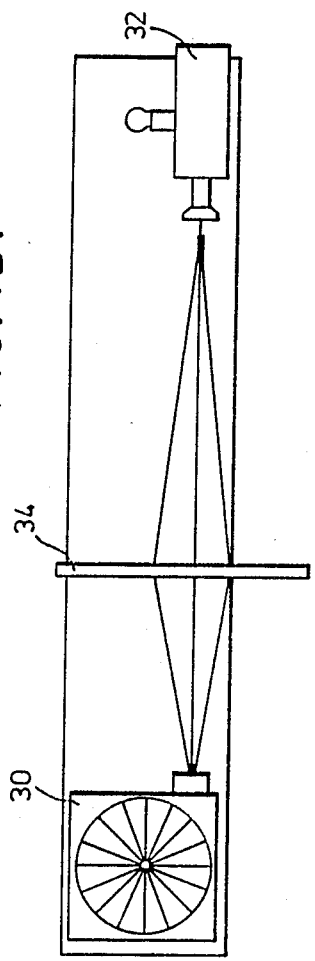

To carry out the analog-to-digital conversion of each X-ray image, an apparatus was constructed for mounting the three principle components used in this process: 1. a standard (Kodak) carousel slide projector fitted with a macro-focus lens; 2. a sheet of neutral-density acetate stretched on a frame, with guide runners; and 3. an Electrohome black-and-white video camera connected to the controlling minicomputer. Seen in FIG. 1, the apparatus is designed as an optical "bench" of sorts, with a projector 30 and camera 32 being fixed in position at opposite ends of the apparatus, and a display screen 34 movable along the projector-camera axis.

Each X-ray is mounted in a glass photographic slide and displayed as a 20 cm wide by 15 cm tall image back-projected on the acetate screen 34 positioned approximately 40 cm in front of the slide projector 30. In this way, the displayed size and focus of each projected image may be controlled by any manipulation of the lens controls of the projector or camera, and the positioning of the projection screen between the two devices.

Each image is digitized as a 512-row and 512-column matrix of values with a range of 0 to 255. At this resolution, it appears that the limiting step in the imaging process is the actual exposure of the radiographic film, and the photographer's abilities and method. Two sources of variation appear to account for the majority of difficulties encountered with current clinical methods, each of which arises from the susceptibility of film radiography to errors produced by human users in a situation that does not lend itself readily to any form of controlled automation (technologically and socially). Variations in patient, film and camera positioning from exposure to exposure, and the requirements for such accurate positioning posed by the process of imaging a small area with a large device from a distance ensure that comparison of images taken at separate times (over years), by separate radiographers will be very difficult. Secondly, small (random) variations in the X-ray beam voltage on exposure, film quality and post-exposure processing induce variations in both the overall intensity and the relative distribution of the 256 possible levels of intensity that can further obscure small changes in tissue between exposures.

Image Processing

Three software processes have been developed for use with pairs of images, in order to: 1. correct spatial transformations of the tissues imaged radiographically as would be evident if the two images were superimposed (spatial alignment), 2. correct brightness and contrast differences due to the above spatial transformations and fluctuations in the radiographic beam intensity, film and processing quality (intensity alignment), and 3. compare two images which have been equalized by the above two processes so as to detect differences between them. The software interface involves the use of a video terminal and keyboard, and a monochrome graphics display and "mouse" pointer. Each process is described below, along with its associated hardware and software.

Spatial Alignment

Hardware

Spatial alignment involves matching of reference points on corresponding areas of each image so that tissue structures that remain constant (evident) on two images may superimpose exactly, or with as little error as possible. Radiographic images provide poor reference markers, as they present indistinct structural features and boundaries, which are unreliable and sensitive to camera positioning error. The alignment process described earlier introduces non-tissue markers that provide sharp, constant reference points with a marker-tissue spatial relationship that can be controlled.

As described earlier, the reference markers preferably consist of lead balls that have been embedded in two perpendicular planes of a bite block modified from those currently used to hold the radiographic film during exposure. Lead is used for maximum density, and balls are used for transformation invariance. (see FIGS. 2 and 3). The X-ray "shadow" produced by the balls is in effect superimposed on that produced by the imaged tissues, as seen in FIG. 5, and thus can serve as artificial reference points that can be used for all exposures of the tissues of interest providing that the relationship between the reference markers and the underlying tissue is maintained for all exposures (i.e., the bite block must be seated on the same teeth in the same position).

In practice, a patient would be fitted with a bite block (or several) at the time of first consultation which would be used for all exposures of the tissues of interest (for which they were first employed). As described, the soft impression of the biting surface of the teeth to be imaged permits accurate positioning on the teeth, to maintain a constant marker-tissue relationship. The spatial arrangement of the reference points allows the best empirical alignment possible with the software algorithm used, appearing as white disks forming two concentric rectangles surrounding the region of interest (see FIG. 4). We currently use a ball diameter of 1/32 inch.

Software

Once the reference and comparison images are digitized, the alignment process consists of three stages: 1. selection of reference points, 2. alignment of reference points on one image to the corresponding points on the other and, by this, all other image points, and 3. repair of image "fractures" caused by the transformations required to accomplish the alignment. Three separate software programs perform the separate stages, although they could be combined into one larger program.

Because the balls present a well-known radiographic appearance, they can be selected with ease by an operator equipped with a mouse pointer that controls a cursor on the monochrome display screen. The operator indicates (with a crosshair cursor) the centre of each reference marker to be used, and the coordinates of the selected point are stored. The sequence of markers selected must remain the same for both images, although there is no empirical effect of overall selection order.

Once reference markers have been chosen, and their spatial coordinates known, the process of alignment is started with the determination of the coordinate differences between each corresponding pair of points. Each difference (along X and Y) is squared and summed and presented to a curve-fitting algorithm that tries to minimize this difference by iterative modifications (transformations) applied to the to-be-matched (TBM) image's reference marker coordinates. The transformations used involve application of (fixed and predetermined) sequences of trigonometric functions to the TBM coordinate values, so as to produce translations along the X- and/or Y-axes, rotations around X-, Y- or Z-axes, and dilation or contraction of the X- and/or Y-axes (see Table 1). The algorithm applies differing amounts of each transformation in turn, and terminates when the lowest possible global image difference is determined (as measured by the sum of squared differences between reference-image marker and TBM-image marker centre coordinates). The parameters used for this "optimal" sequence of transformations are stored and applied to every point on the TBM image. In essence, the program determines the best way to shift, rotate, expand or contract the TBM image, so that its markers best superimpose on those of the "standard" image and then apply these operations to every other point on the TBM image.

TABLE 1

| Alignment models tested Each model is composed of two or three successive transformations: | |
|---|---|
| Model 1: | (1) Translation along X- and Y-axes |
|  | (2) Rotation around Z-, Y-, and X-axes |
| Model 2: | (1) Translation along X- and Y-axes |
|  | (2) Rotation around Z- and Y-axes |
|  | (3) Dilation (size change) of X- and Y-axes |
| Model 3: | (1) Perspective transformation with manipulation of |
|  | - viewing projection, and |
|  | - projection plane |
|  | (2) Rotation around Z-, Y-, and X-axes |
| Model 4: | (1) Translation along X- and Y-axes |
|  | (2) Dilation (size change) of X- and Y-axes |
|  | (3) Rotation around Z-axis |

Because of limits on computational precision and image resolution, and differences in camera distancing from the tissues, the transformed image may contain regions for which no discrete transformed point can be calculated. For example, a TBM image that is smaller than the reference (or initial) image will require fractional expansion for proper alignment, and the floating-point coordinates used to represent each new image coordinate pair are rounded up or down to the nearest integer for display. This error would appear as a pattern of no-intensity horizontal, vertical and/or diagonal lines (solid or broken) of one unit width superimposed on the transformed image. For all transformations performed to-date (and those expected), these lines can be easily removed by writing to each nointensity point the average of its (up to eight) nearest non-zero neighbors.

Once the spatially-transformed image has been computed, it can be stored in place of the TBM image, as it will represent the best spatial fit of that image to the reference image. The pair of images to be compared can then be further manipulated for purposes of enhancement (perhaps to increase contrast or definition), or in some cases may be amenable to immediate comparison. It has been found, however, that an additional source of image differences, unrelated to pathological differences and resulting from inadequacies in the technology and practice of film-screen radiography, often necessitate an additional stage of image equalization before proper comparison and measurement may be performed.

Intensity Alignment

Software

After spatial alignment, and before comparison, images must be equalized for variations in exposure duration, film response, and processing controls. One program controls this alignment stage with little operator intervention. The frequency distribution of intensity levels of each image is calculated and converted into a relative frequency distribution. These distributions in turn can then be converted into probability density functions for each image by calculating a cumulative frequency distribution. The probability density function determined for each image can then be transformed to fit an "ideal" (specified) distribution, and the image's new frequency distribution can be reconstituted. Currently, the ideal distribution is a pseudo-sigmoidal function with those image points in the top or bottom 5% of the frequency distribution set to their respective extremes, and the intermediate 90% of the distribution fit to a linear function with a slope of 1 (see FIG. 5). An alternate distribution currently being tested is the gamma probability density function, which, when its parameters are set appropriately, assumes a shape much like that found empirically with X-ray images (i.e., a positively-skewed quasi-normal distribution of positive values), and thus can effect an initial, equalizing, fit with fewer and smaller intensity-value transformations than distributions with other forms.

Once this final phase of image equalization has been accomplished, the two images can be compared with a minimum of non-pathological image difference. Other operations can also be enacted on the images prior to comparison. Further intensity distribution manipulations may be used to highlight selected corresponding regions on each image (e.g., fitting to normal, exponential or sigmoidal curves). Image "definition" may be enhanced to show detail, or reduced to remove "grain".

Image Comparison

Subtraction of one image from another is the most straightforward process by which images can currently be compared. An informal method, involving rapid display of each of a pair of images in succession, can be used for an initial and easily-recognized visual identification of obvious differences. For quantifiable differences, however, more sophisticated methods must be employed, and this display-oriented method will not be discussed further.

One central subtraction method is currently used to perform all comparisons (on pairs of images), although several analytic software routines are available to provide parameters controlling the subtraction operation. As was done for the spatial alignment transformations, a "reference" image is selected; for comparison, the oldest of a pair of exposures would usually be considered for this role. The intensity of each comparison-image point is subtracted from the intensity of its corresponding point in the reference image.

Figure 6:
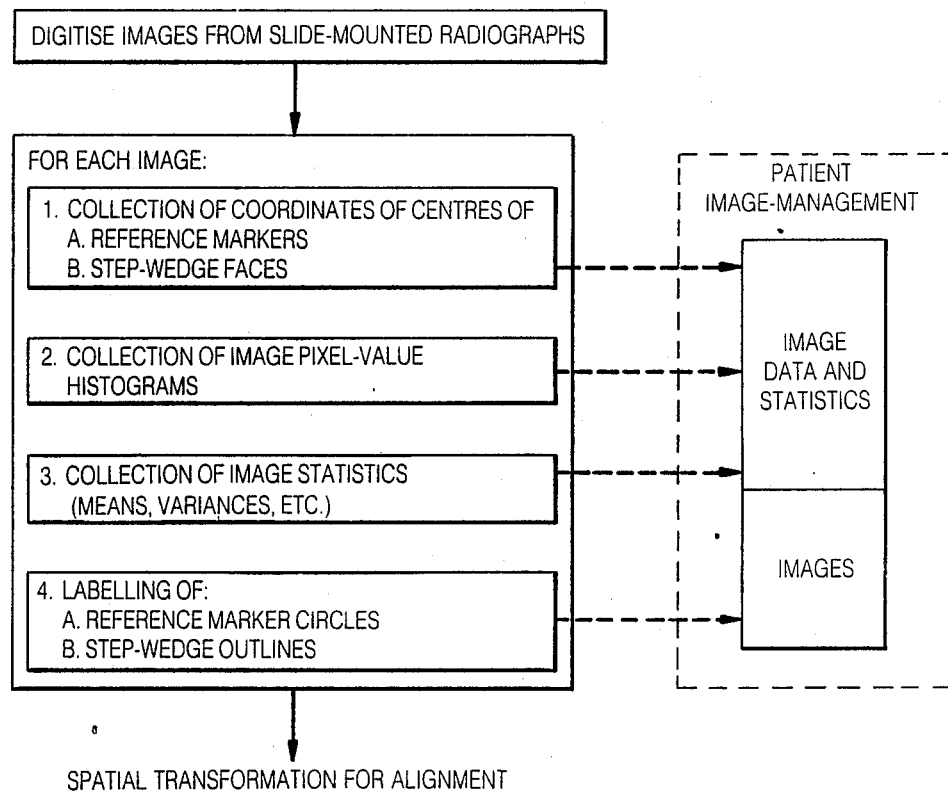
Figure 7:
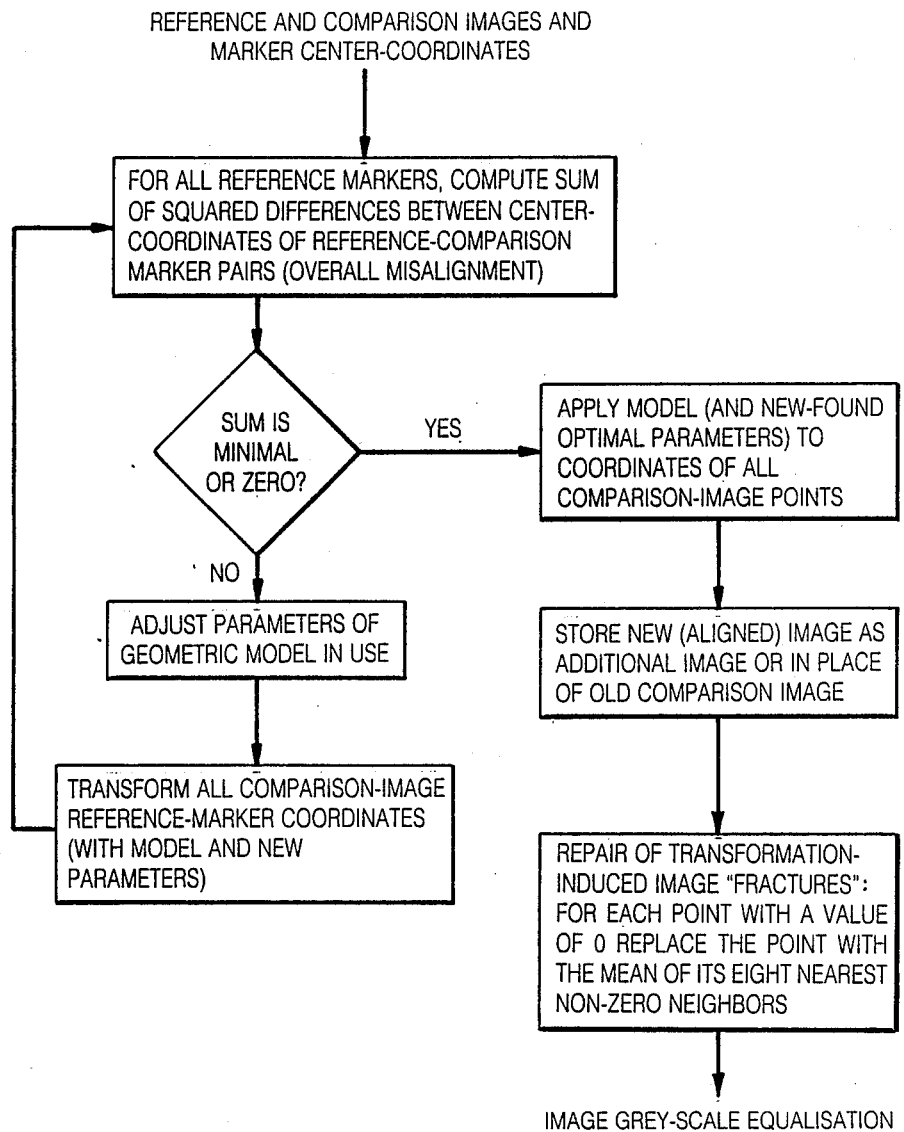
Figure 8:
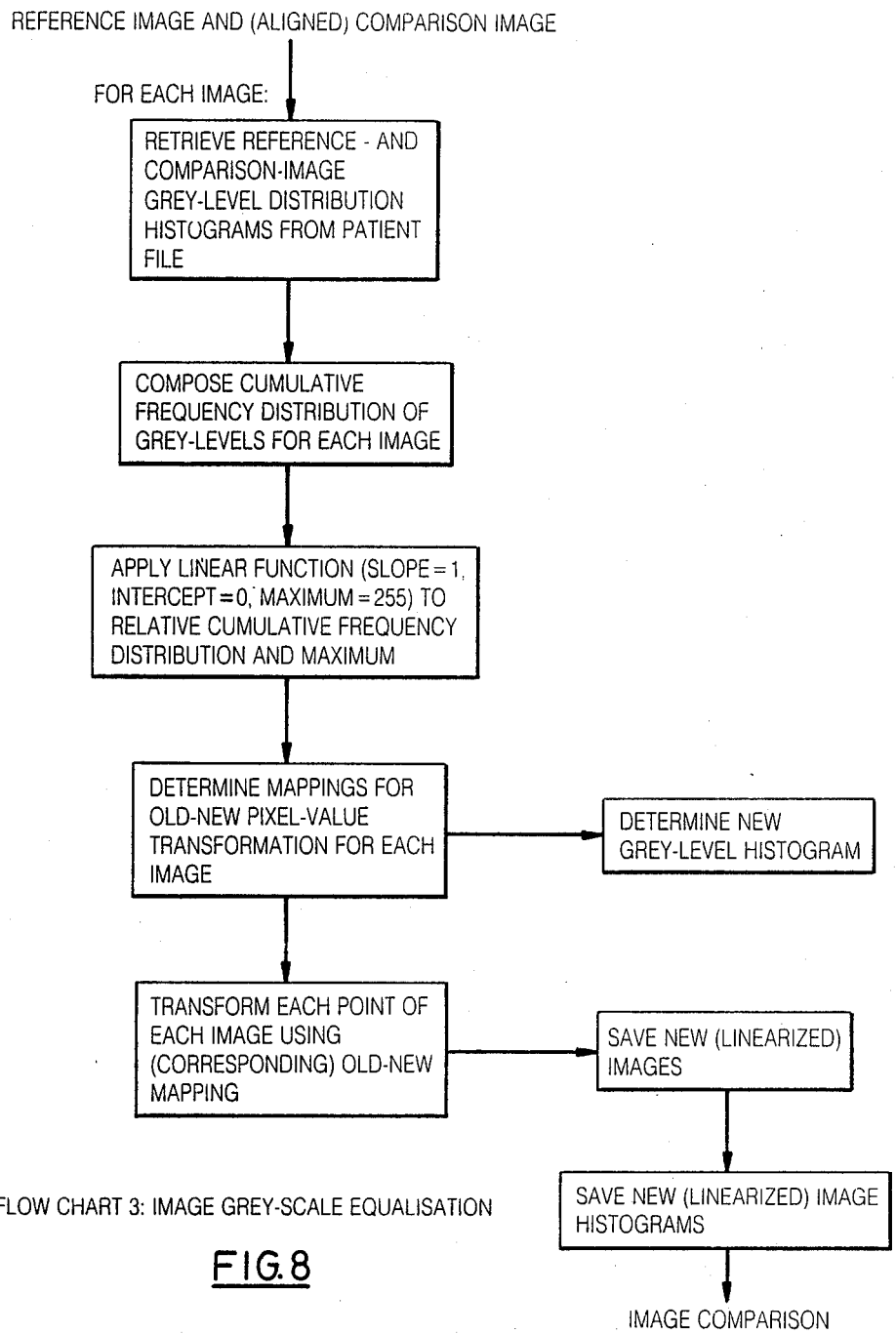
Figure 9:
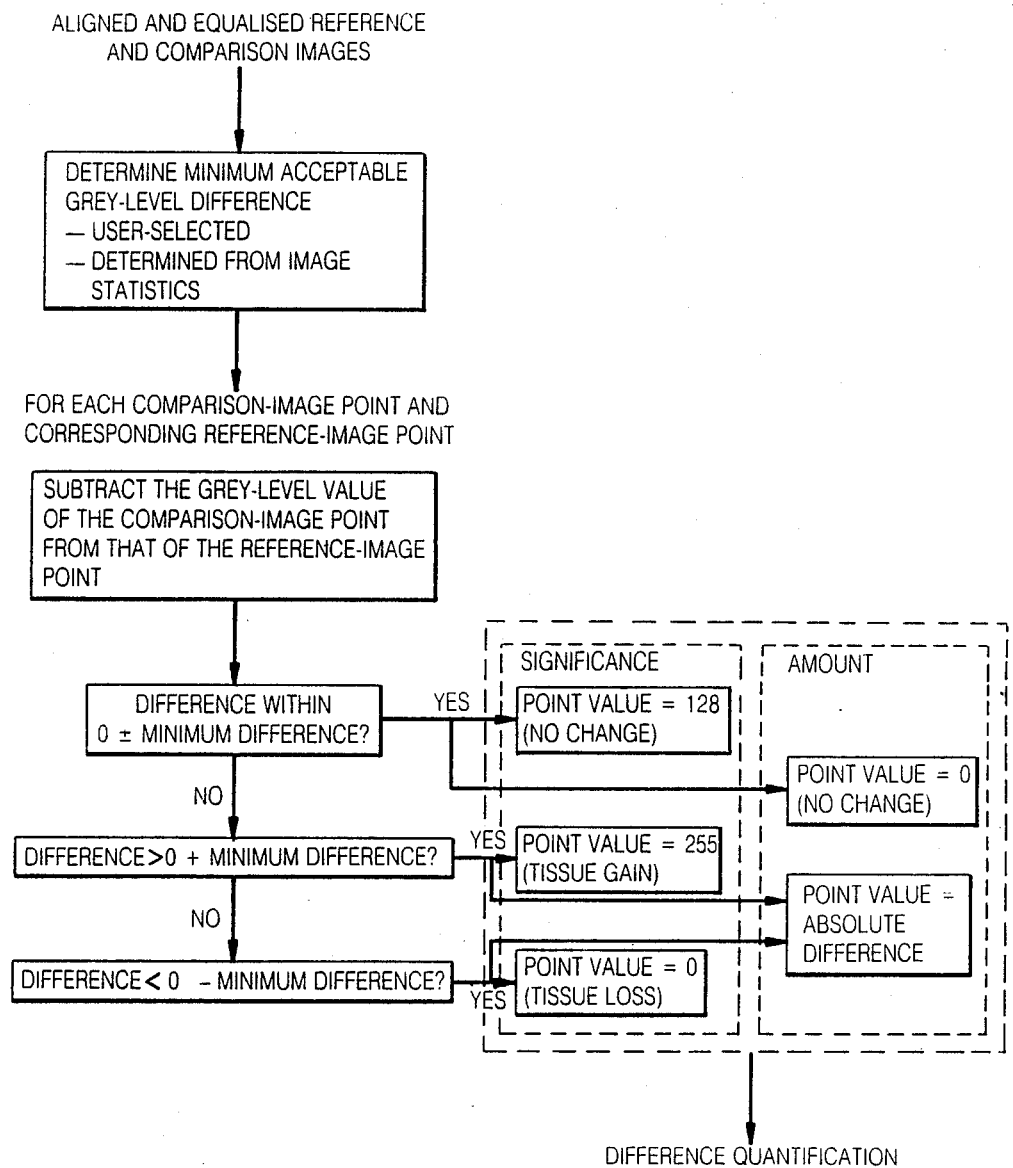
Figure 10:
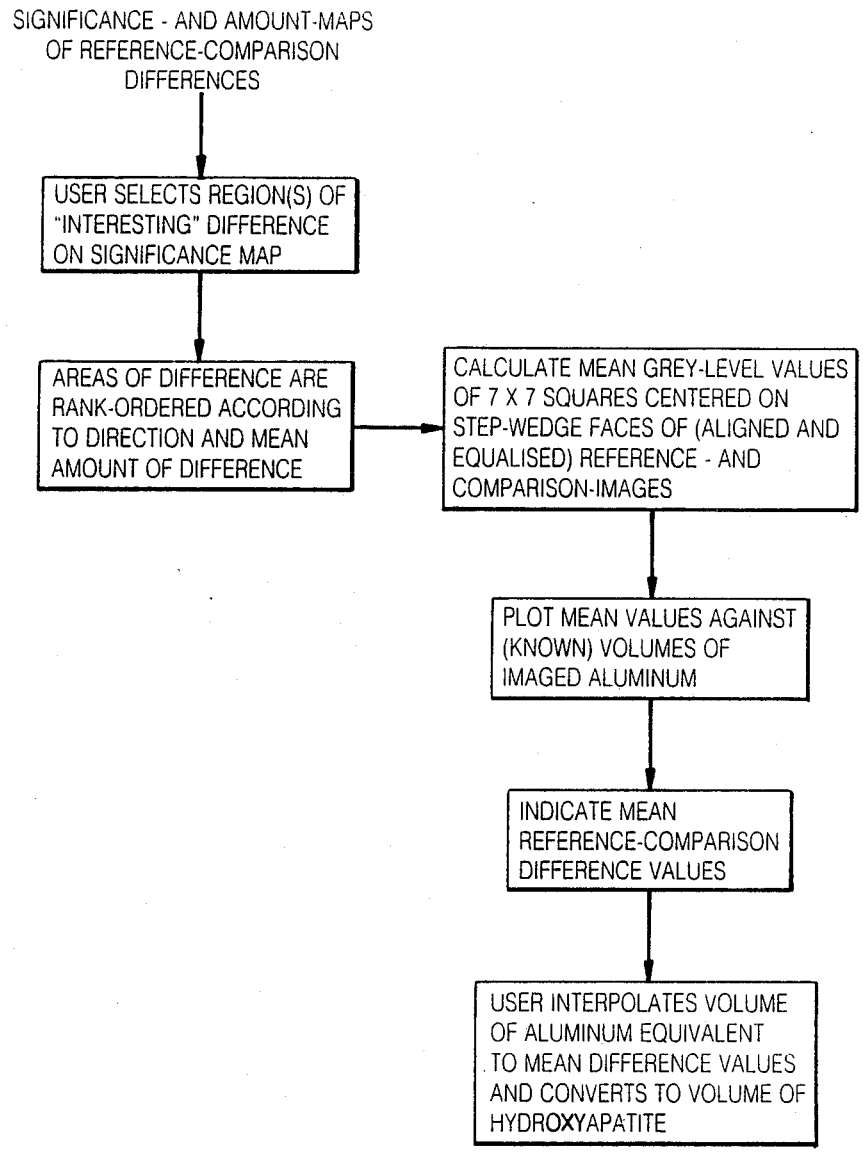

The subtraction produces at each point one of three classes of values: positive, negative and zero indicating, respectively, tissue gain, tissue loss, and no tissue change (see FIG. 6). The resulting "difference" image can be displayed directly (as an image of absolute differences) or coded to reflect the result of the subtraction at each point, with tissue gain appearing as high intensity (white), loss appearing as low intensity (black) and no change appearing as medium intensity (grey). Because the image equalizations performed are still subject to operator error or calculation and display limits, a certain margin of error remains that may hinder measurement of true differences. For this reason the subtraction process can be constrained by limits on the amount of numeric difference between subtracted points that is considered acceptable and to be ignored by the measurement software.

Several methods can be used to determine those intensity changes that are considered to be nonsignificant and, conversely, those that exceed a particular threshold. The simplest, and thus first introduced, method will involve operations on the distribution of image-pair differences resulting from subtraction (centered on 0 and ranging from 0–255 positively and negatively): specifically, the use of the distribution's standard deviation (or 5th and 95th percentiles) to determine the upper and lower thresholds for "difference".

Measurement of Change

Once suitable limits on point differences have been established, only those pairs of image points that are found to differ "significantly" (gain or loss) will be considered for further analysis. It is expected that further enhancement will be required to constrain the search for significant differences to specific image regions, and to exclude areas of difference smaller than those of clinical interest (e.g., scattered unitary points).

Once the final regions of difference have been localized, their absolute difference can then be related to a recognized measure of tissue density. The step-wedge located at the top of each image can be used as a reference density with which all pathological tissue densities can be compared.

The operator, again using the mouse pointer and the screen cursor as for spatial alignment, selects the center of each grey square presented by the step-wedges of the reference and TBM images. The average of all intensities in a $N \times N$ unit square centered on the point selected by the operator is used as the intensity value of the selected point. This averaging is performed to remove noise introduced by the film's grain, and minimize intensity variations remaining after all equalizing transformations.

Once all points have been chosen, a mean value for each step-wedge density is calculated from the values presented by each image, and these values are used to determine the particular function that characterizes the relationship between step-wedge density and resulting intensity level. When this function (and its parameters) have been determined, the mean difference of the area or areas that have been marked as significantly different is then translated into a specific density of aluminum. A standard empirical relationship can then be used to translate the aluminum-density value into a value of hydroxyapatite-density, a widely-used density metric.

In FIG. 5, the exposed processed film shows the shadows 40 of the lead reference balls, along with the skeletal bone 42, the individual teeth 44, and the image of the step-wedge 46.

In FIG. 5, part (a) is a pre-lesion radiograph, and part (b) is a post-lesion radiograph. In the image (b), a first arrow 50 points to the bottom edge of the image, above which a demineralization location is found about one third of the way up. The arrow 52 shows a remineralization location, again about one third of the way up.

FIG. 5 (c) shows an idealized subtraction image, where the black portion 54 indicates loss of tissue, whereas the white portion 56 shows tissue gain. The remainder of the image (c) shows no change.

While one embodiment of this invention has been illustrated in the accompanying drawings and described hereinabove, it will be evident to those skilled in the art that changes and modifications may be made therein without departing from the essence of this invention, as set forth in the appended claims.

The embodiments of the invention in which an exclusive property or privilege is claimed are defined as follows:

1. In a diagnostic process for tissue structure in or close to human teeth, in which two X-ray images are made on photosensitive film of the same structure at the beginning and the end of a time interval during which the structure may change, a method of permitting a computing device which electronically stores the images to perform operations on the images as reproduced in the form of pixels on a monitor screen, each pixel having a specific grey level, the method comprising providing, when each of the images is made, a particular 3-dimensional spatial pattern of spherical marker elements in a particular juxtaposition to said structure so that the shadows of the elements arise on the respective images, the said juxtaposition being the same for each image, the marker elements being separated balls incorporated in a bite block, the X-radiation passing in order through the teeth, the marker elements, and the film.

2. The invention claimed in claim 1, in which the balls are of lead, a portion of the lead balls being all substantially in the same plane aligned with the plane of the film.

3. The invention claimed in claim 1, in which the balls are of lead, a portion of the lead balls being all substantially in a first plane aligned with and close to the plane of the film, and the remaining lead balls being positioned in a second plane at right angles to the first plane.

4. The invention claimed in claim I, in which the bite block incorporates an aluminum step wedge to allow the computing device to align the grey scales of the two images.

5. For a diagnostic process in which two radiographic images are made on radiographic film of the same human tissues within or close to the teeth at the beginning and the end of a time interval during which tissue change may occur, a bite block for permitting a computing device which electronically stores the images to perform operations on the images as reproduced in the form of pixels on a monitor screen, each pixel having a specific grey level, the bite block registering repeatedly with the same teeth of a given person and incorporating a specific, 3-dimensional spatial pattern of spherical marker elements so that when the bite block is held between the given person's teeth the elements will have a specific and repeatable juxtaposition with respect to the dental structure and the shadows of the elements will arise on the respective radiographic films.

6. The invention claimed in claim 5, in which said marker elements are lead balls contained within a fixed portion of the bite block.

7. The invention claimed in claim 5, in which said marker elements are lead balls of which at least a portion are all substantially in the same plane aligned with and close to the plane of the film.

8. The invention claimed in claim 5, in which the marker elements are metallic balls, a portion of the metallic balls being all substantially in a first plane aligned with and close to the plane of the film, and the remaining metallic balls being positioned in a second plane normal to the first plane.

9. The invention claimed in claim 5, in which the bite block incorporates an aluminum step wedge to allow the computing device to align the grey scales of the two images.

10. A method for investigating changes in animal tissues, which are within or close to human teeth, comprising:
at a first point in time, providing a bite block containing a plurality of spherical marker elements in a specific, 3-dimensional spatial arrangement, said bite block being gripped in a reproducible fashion at a given location between the teeth so as to ensure that the marker elements achieve a repeatable, 3-dimensional juxtaposition with respect to the tissues, and making a first radiographic image of the tissues by exposing a first photosensitive film to X-ray radiation that has first passed through both the tissues and the marker elements, so that the shadows of the marker elements appear superimposed on the first image of the tissues,
at a later point in time, causing the bite block to be gripped again in said reproducible fashion at said given location between the teeth so as to ensure that the marker elements achieve the same 3-dimensional juxtaposition with respect to the tissues, and making a second radiographic image of the tissues by exposing a second photosensitive film to X-ray radiation that has first passed through both the tissues and the marker elements, so that the shadows of the marker element s appear superimposed on the second image of the tissues,
converting the first and second images to first and second arrays of pixels and storing the pixel arrays electronically in a memory means, wherein each pixel has a pair of geometric coordinates and also an index number identifying its grey level,
using a computing device to improve the alignment of one array of pixels with respect to the other, wherein the computing device identifies the shadows of the marker elements in the two pixel arrays, and operates on one array in such a way as to bring the geometric coordinates of the shadows on one array into the closest possible coincidence with the geometric coordinates of the shadows on the other array, by causing said one array to undergo one or more of the operations of:
(a) translation,
(b) rotation,
(c) scaling up,
(d) scaling down,
(e) differential scaling,
storing the improved pixel array electronically in the memory means,
and assessing the intensity differences between pairs of corresponding pixels in the improved array and the said other array to determine whether tissue change is indicated.

11. The invention claimed in claim 10, in which a first portion of the metallic balls is substantially in a single plane aligned with and close to the plane of the film, and a second portion of the metallic balls is aligned in a plane perpendicular to said first-mentioned plane.

12. The invention claimed in claim 10, in which the marker elements are lead balls.

13. The invention claimed in claim 10, in which the bite block incorporates a step wedge, and wherein the computing device utilized the images of the step wedge on the two pixel arrays to align the grey scales of the arrays.

* * * * *